United States Patent [19]

Stanier

[11] Patent Number: 5,964,937
[45] Date of Patent: Oct. 12, 1999

[54] AMORPHOUS SILICAS

[75] Inventor: Peter William Stanier, Cheshire, United Kingdom

[73] Assignee: Crosfield Limited, Warrington, United Kingdom

[21] Appl. No.: 08/996,867

[22] Filed: Dec. 23, 1997

Related U.S. Application Data

[63] Continuation of application No. PCT/EP96/02535, Jun. 10, 1996.

[30] Foreign Application Priority Data

Jun. 30, 1995 [EP] European Pat. Off. ............ 95304614

[51] Int. Cl.$^6$ ............................ C01B 33/18; C01B 33/12
[52] U.S. Cl. .......................... 106/492; 106/483; 423/339
[58] Field of Search .................................. 106/483, 492; 423/335, 339

[56] References Cited

U.S. PATENT DOCUMENTS

| | | | |
|---|---|---|---|
| 3,428,425 | 2/1969 | Marotta | 423/339 |
| 4,191,742 | 3/1980 | Wason et al. | 424/49 |
| 4,230,765 | 10/1980 | Takahashi et al. | 428/292.1 |
| 4,243,428 | 1/1981 | Donnet et al. | 106/492 |
| 4,244,707 | 1/1981 | Wason | 51/308 |
| 4,312,845 | 1/1982 | Wason | 423/339 |
| 4,330,519 | 5/1982 | Takahashi et al. | 423/335 |
| 4,435,380 | 3/1984 | Pader . | |
| 4,992,251 | 2/1991 | Aldcroft et al. | 423/335 |
| 5,035,879 | 7/1991 | Aldcroft et al. | 424/49 |
| 5,108,734 | 4/1992 | Colodney et al. | 424/49 |
| 5,120,528 | 6/1992 | Chang et al. | 424/49 |
| 5,225,177 | 7/1993 | Wason et al. | 423/339 |
| 5,342,598 | 8/1994 | Persello | 423/339 |
| 5,447,704 | 9/1995 | Aldcroft et al. | 423/339 |
| 5,512,271 | 4/1996 | McKeown et al. | 424/49 |
| 5,624,652 | 4/1997 | Aldcroft et al. | 423/335 |
| 5,647,903 | 7/1997 | McGill et al. | 424/49 |
| 5,651,958 | 7/1997 | Rice | 424/49 |

FOREIGN PATENT DOCUMENTS

| | | |
|---|---|---|
| 0 139 754 | 5/1985 | European Pat. Off. . |
| 0 272 380 | 6/1988 | European Pat. Off. . |
| 0 368 130 | 5/1990 | European Pat. Off. . |
| 1 598 233 | 9/1981 | United Kingdom . |
| A 92/02454 | 2/1992 | WIPO . |

*Primary Examiner*—Robert H. Harrison

[57] ABSTRACT

An amorphous silica having an RDA value of between 30 and 70, an oil absorption capacity of between 100 and 155 cc/100 g and a moisture loss of less than 7% w/w, can be incorporated at a 10% to 25% loading into a transparent toothpaste having a refractive index of above 1.445, this toothpaste having an RDA value of between 30 and 60.

19 Claims, No Drawings

AMORPHOUS SILICAS

This is a continuation under 35 U.S.C. section 120 of PCT application PCT/EP96/02535 which designated the United States, filed internationally on Jun. 10, 1996.

FIELD OF THE INVENTION

The present invention relates to amorphous silicas particularly used as abrasives in oral compositions. More particularly, the present invention relates to amorphous precipitated silicas with good cleaning properties associated with low abrasion characteristics. The present invention further relates to a process for the production of such silicas and to oral compositions containing such silicas.

BACKGROUND OF THE INVENTION

Toothpaste compositions are well characterised in the literature and many compositions are disclosed in patent specifications and other literature. Toothpaste compositions contain a number of specific components for example abrasive agents, fluoride sources, binders, preservatives, humectants, anti plaque agents, colouring agents, water, flavour and other optional ingredients.

Of these components the abrasive agent is required to provide the appropriate cleaning and plaque removal without subjecting the tooth itself to excessive abrasion. Typically a toothpaste composition will contain from about 5% to about 50% preferably up to about 30% by weight of abrasive. Commonly used abrasives are aluminas, calcium carbonates and calcium phosphate. More recently synthetic silicas have been adopted because of their efficient cleaning, compatibility with other ingredients and their physical properties.

An important property of a silica for use in toothpaste formulations is its oil absorption capacity. For silicas of similar particle size, this property directly relates to the thickening effect obtained when adding the silica into a toothpaste formulation, the higher the oil absorption capacity the higher the observed thickening effect. Therefore the higher the oil absorption capacity, the lower the volume of silica which can be incorporated into the toothpaste composition, something which limits the toothpaste formulation. Moreover, the higher the oil absorption, the weaker the structure.

Another important property of a silica for use in toothpaste formulations is its ability to provide the appropriate stain and plaque removal (herein after referred to as the cleaning capacity) without subjecting the tooth itself to excessive abrasion i.e. without damaging dentine or enamel. Normally the cleaning capacity is correlated with the abrasion properties. The concept of preventing stain build-up on a tooth surface must be distinguished from stain removal, which is a considerably more difficult task. A proteinaceous pellicle film forms continuously on teeth and through staining with food and drink can become coloured. If this is allowed to build up with time, the coloured pellicle becomes considerably thicker and more mineralised than the 12–24 hour film and consequently more difficult to remove. Normal dental abrasives are fully capable of controlling 12–24 hour pellicle, but are relatively ineffective at removing old stain.

Another important property of a silica for use in transparent toothpaste formulations is its apparent refractive index. Any transparent toothpaste can be characterised by its refractive index, when incorporating an abrasive material into a transparent toothpaste it is important that this abrasive material remains invisible, i.e. that the clarity of the toothpaste remains the same. This is achieved only if the abrasive material has an apparent refractive index which matches the refractive index of the toothpaste. Now, toothpastes can have refractive indices ranging from 1.430 to 1.470. A refractive index of above 1.445 is generally considered as a high refractive index.

Toothpastes in the form of clear gels are now proposed to consumers, some of those gels being absolutely water white. The method for assessing clarity in this invention involves use of a standard chart consisting of black symbols varying in size on a white background. This is the RIT Alphanumeric Resolution Test Object, RT 4-74, produced by Graphic Arts Research Center, Rochester Institute of Technology. The ability to discern the symbols clearly through a sample of product of standard thickness (1 cm) is measured. The symbols are numbered from –12 to +13. The higher, more positive the number, the greater the clarity. In the present invention a number of 0 or above is considered to be characteristic of a visually clear toothpaste.

In U.S. Pat. No. 5,225,177 is claimed an amorphous silica having a moisture of 10%, a 5% pH of 7, an oil absorption of less than 125 cc/100 g, a refractive index of 1.45. It is further stated that the precipitated silicas according to this document have an RDA value of at least 40, preferably 70 to 120. A detailed description of the method used for measuring the RDA value is provided and under 'E. Test Run' it is clear that the RDA value which is given is not the RDA of the silica but the RDA of a toothpaste containing this silica. Moreover on column 11 under 'Calculations' it is made clear that the RDA values are given 'for a particular paste'. Now, It is not disclosed what is the nature of the toothpaste and, more importantly, the toothpaste silica loading is not disclosed (6% to 35% according to column 5 line 25). The RDA values therefore refer to the abrasion property of an unknown toothpaste containing an unknown amount of a specific amorphous silica and it is not possible, relying on U.S. Pat. No. 5,225,177 to know what is the RDA value of the silica.

Now, the applicant of U.S. Pat. No. 5,225,177 is marketing a product called Zeodent 115 (Average particle size 9.3 $\mu$m, refractive index 1.45, oil absorption 110 cc/100 g) which is believed to be the silica disclosed in U.S. Pat. No. 5,225,177. The RDA value of this silica is 97 which is regarded as a low to medium abrasive silica.

Commercially available silicas can be broadly categorised as low abrasion if less than 90 RDA and medium abrasion if between 110–150 RDA. Samples of commercially available toothpaste silicas were submitted to Missouri Analytical Laboratories and the RDA value of the silica was determined with the following results:

| SILICA NAME | RDA |
| --- | --- |
| ZEODENT 113 | 84 |
| ZEODENT 115 | 97 |
| TIXOSIL 73 | 83 |
| SIDENT 9 | 113 |
| SIDENT 12 | 91 |
| SORBOSIL AC77 | 125 |
| SORBOSIL AC35 | 110 |

(NB: Zeodent, Tixosil, Sident and Sorbosil are registered trade marks of Huber, Rhone Poulenc, Degussa and Crosfield respectively).

From the data, it can be seen that even current low abrasion silicas have relatively high RDA values and there is a need for an amorphous silica having a much lower RDA value which, when incorporated into an oral composition, maintains good cleaning characteristics. There is also a need for such an amorphous silica which does not alter the clarity of the toothpaste composition to which it is added.

TESTS AND DEFINITIONS i) Oil Absorption

The oil absorption is determined by the ASTM spatula rub-out method (American Society Of Test Material Standards D, 281).

The test is based on the principle of mixing linseed oil with the silica by rubbing with a spatula on a smooth surface until a stiff putty-like paste is formed which will not break or separate when it is cut with a spatula. The volume of oil used is then put into the following equation:

$$\text{Oil absorption} = \frac{\text{cm}^3 \text{ oil absorption} \times 100}{\text{Wt. of silica sample in g}}$$

$$= \text{cm}^2 \text{ oil/100g silica}$$

ii) Weight Mean Particle Size

The weight mean particle size of the silica is determined using a Malvern Mastersizer model X, with a 45 mm lens and MS15 sample presentation unit. This instrument, made by Malvern Instruments, Malvern, Worcestershire uses the principle of Fraunhoffer diffraction, utilising a low power He/Ne laser. Before measurement the sample is dispersed ultrasonically in water for 7 minutes to form an aqueous suspension.

The Malvern Mastersizer measures the weight particle size distribution of the silica. The weight mean particle size ($d_{50}$) or 50 percentile, the 10 percentile ($d_{10}$) and the 90 percentile ($d_{90}$) are easily obtained from the data generated by the instrument.

iii) Loose Bulk Density

Loose bulk density is determined by weighing approximately 180 ml of silica into a dry 250 ml measuring cylinder, inverting the cylinder ten times to remove air pockets and reading the final settled volume.

$$\text{Loose bulk density} = \frac{\text{Weight}}{\text{Volume}} \times 100 \text{ g/l}$$

iv) Electrolyte Levels

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

v) Moisture Loss at 105° C.

Moisture loss is determined by the loss in weight of a silica when dried to constant weight in an electric oven at 105° C.

vi) Ignition Loss at 1000° C.

Ignition loss is determined by the loss in weight of a silica when ignited in a furnace at 1000° C. to constant weight.

vii) Structural Water Content

Structural water content is defined by the difference between the ignition loss at 1000° C. and the moisture loss at 105° C.

viii) pH

This measurement is carried out on a 5% w/w suspension of the silica in boiled demineralised water ($CO_2$ free).

ix) BET Surface Area

Surface area is determined using standard nitrogen adsorption methods of Brunauer, Emmett and Teller (BET), using a single point method with a Sorpty 1750 apparatus supplied by Carlo Erba company of Italy. The sample was outgassed under vacuum at 270° C. for 1 hour before measurement.

x) Radioactive Dentine Abrasion Test (RDA)

The procedure follows the method for assessment of dentifrice abrasivity recommended by the American Dental Association (Journal of Dental Research 55 (4) 563, 1976). In this procedure extracted human teeth are irradiated with a neutron flux and subjected to a standard brushing regime. The radioactive phosphorous 32 removed from the dentin in the roots is used as the index of the abrasion of the dentifrice tested. A reference slurry containing 10 g of calcium pyrophosphate in 50 ml of 0.5% aqueous solution of sodium carboxymethyl cellulose is also measured and the RDA of this mixture is arbitrarily taken as 100. The precipitated silica to be tested is prepared as a suspension of 6.25 g in 50 ml of 0.5% aqueous solution of sodium carboxymethyl cellulose and submitted to the same brushing regime.

When testing pastes, 25 g of paste dentifrice are added to 50 ml of water.

xi) Mercury Intrusion Volume

Mercury intrusion volumes are determined (in $cm^3/g$) by standard mercury intrusion procedures using a Micromeritics Autopore 9220 mercury porosimeter. The pore radius is calculated from the Washburn equation using values of surface tension for mercury of 485 dynes/cm and contact angle of 140°.

Prior to measurement the sample was outgassed at room temperature to a pressure of 50 microns of mercury.

Mercury pore volume can be split into two components: intra and inter particle porosity. The inter particle porosity is a measure of the packing of the aggregated structure and is influenced by particle size. The intra particle porosity of a silica is a measure of the porosity of the fundamental particles and is determined by the wet processing conditions.

The mercury intrusion volume recorded is that occurring over the range of calculated pore diameters of 0.05 to 1.0 micron to represent the true intra-particle porosity of the silica from the mercury intrusion curve, i.e. the porosity of the voids within the particles.

xii) Refractive Index (RI)/Transmission

The sample of silica is dispersed in a range of Sorbitol syrup (70% Sorbitol)/water mixtures. After de-aeration, usually 1 hour, the transmission of the dispersions is determined using a spectrophotometer at 589 nm; water being used as blank. The refractive index of each dispersion is also measured using an Abbe refractometer.

A graphical representation of transmission plotted against refractive index allows the range of refractive indices over which the transmission exceeds 70% to be determined. The maximum transmission of the sample and the apparent refractive index of silica at which this is obtained can also be estimated from this graph.

xiii) Mean Pore Diameter (MPD):

This parameter is related to the surface area and pore volume and, using a cylindrical model, is calculated for a silica product with the formula:

$$MPD \text{ (in nm)} = \frac{\text{pore volume (in } cm^3/g) \times 4000}{\text{surface area (in } m^2/g)}$$

Pore volume is the mercury intrusion volume defined in xi).

xiv) Skeletal Density using Helium Pycnometry

The skeletal density of silica samples is determined using a Micromeretics Accupyc 1330 pycnometer. Before measuring the samples the instrument is calibrated with helium. Sufficient measurements (usually 3) are carried out to allow an accurate calculation of the chamber volume and "dead space" in the apparatus. Measurement of the samples is a repeat of the calibration routine but first the samples are dried at 120° C. for two hours prior to analysis. The calibrated empty volume of the pycnometer has been determined. For each analysis, a sample of known weight is placed in the chamber and the measurement is made automatically.

General Description of the Invention

It is a first object of the present invention to provide an amorphous silica characterized by:

an RDA value of between 30 and 70, preferably between 40 and 70, more preferably between 50 and 60.

an oil absorption capacity of between 100 and 155 $cm^3$/100 g, preferably between 100 and 145 $cm^3$/100 g, preferably between 115 and 130 $cm^3$/100 g, Advantageously, the amorphous silicas of the invention present a moisture loss of less than 10% w/w, preferably less than 7% w/w, more preferably less than 6% w/w, even more preferably less than 5%.

It has been found that silicas with an oil absorption of above 155 $cm^3$/g and an RDA of below 70 presented a too weak structure to operate as proper stain prevention agents.

Preferably, the amorphous silica of the invention is a precipitated silica.

Preferably also, the amorphous silica of the invention presents a light transmission of more than 70% at a refractive index within the range of 1.445 to 1.456. Most preferably, the amorphous silica of the invention presents a peak of light transmission in the refractive index range of 1.445 to 1.456. This enables the silica to be incorporated into transparent oral compositions of high refractive indices.

Toothpaste abrasives have low intra particle porosity, since they have dense structures with high strength. Silicas of the invention have a suprisingly high intra-particle mercury pore volumes for silicas which give good cleaning in dental formulations. More specifically, amorphous silicas of the invention present a mercury pore volume of above 1 $cm^3$/g, preferably above 1.2 $cm^3$/g, more preferably below 1.6 $cm^3$/g.

The high mercury pore volume is accompanied by a relatively high Mean Pore Diameter, typically between 25 and 100 nm, preferably above 40 nm. This high mercury pore volume and this high mean pore diameter means that the silica of the invention presents a relatively low BET surface area of 50 to 200 $m^2$/g, preferably between 50 and 150 $m^2$/g.

The amorphous silica of the invention presents a structural water content of between 3.5% and 5.0%, preferably between 4.0 and 4.5%, a pH in a 5% solution of between 6 and 7.5, a loose bulk density of between 180 and 300 g/l, preferably between 200 and 250 g/l, a skeletal density of above 2.1 $g/cm^3$ and a Weight Mean Particle Size of between 3 and 20 $\mu$m, preferably between 5 and 15 $\mu$m.

It is a second object of the present invention to provide a process for the production of amorphous silicas comprising:

adding a 17.0 to 21.5% w/w solution of 2.1 to 2.5 Molar Ratio silicate solution to water, then further adding a 17.0 to 21.5% w/w solution of 2.1 to 2.5 Molar Ratio silicate solution together with a 15 to 20% w/w sulfuric acid solution, over a period of over 40 minutes, preferably less than 80 minutes, at such flow rates that the pH is maintained in the range from 8.0 to 9.0, then aging the resultant slurry for a period of 0 to 30 minutes, preferably for 8 to 12 minutes, at a temperature of 90° C. to 100°, doing a second addition of a 15 to 20% w/w sulfuric acid solution to bring the pH down to pH 3 to 5.

aging the resulting the slurry for a period of 0 to 20 minutes, preferably for 8 to 12 minutes, at pH 5 at a temperature of between 90 and 100° C., adjusting the pH to pH 3.5 to 5, eventually filtering, washing and drying the final slurry.

It has been found that silicas obtained through this process present good cleaning characteristics without damaging the teeth and are particularly good at preventing stain formation.

It is a third object of the present invention to provide an oral composition comprising an amorphous silica, said amorphous silica having:

an RDA value of between 30 and 70, preferably between 40 and 70, most preferably between 50 and 60, an oil absorption capacity of between 100 and 155 $cm^3$/100 g, preferably between 100 and 145 $cm^3$/100 g, most preferably between 115 and 130 $cm^3$/100 g, Preferably, the amorphous silica presents a moisture loss of less than 10% w/w, preferably less than 7% w/w, more preferably less than 6%, most preferably less than 5% w/w.

Preferably the oral composition is a visually clear toothpaste composition having a refractive index of above 1.445, preferably above 1.45, comprising 5 to 25% by weight, preferably 10 to 25% by weight, of the amorphous silica according to the present invention, said toothpaste composition having an RDA of 30 to 60, preferably above 35, more preferably up to 50.

This toothpaste composition is capable of maintaining clean human teeth without damaging said teeth.

In the oral compositions according to the present invention, the level of the amorphous silica may be wide ranging, for example depending upon the physical form of the desired end product.

Compositions according to the invention may be solids, e.g. similar in form to conventional tooth powders, or pastes, creams or gels, e.g. like conventional toothpastes, or possibly even liquids.

Particularly preferred compositions of the invention are in the form of pastes, gels, creams or liquids, the exact physical properties of which may be controlled for example by suitable adjustment of the solid to liquid ratio and/or the viscosity of the liquid phase, e.g. by selecting appropriate contents of adjunct components, as described further below.

In preferred embodiments of the invention, the amorphous silica of the invention is present in the composition in an amount of from about 1 to about 99% by weight, more preferably from about 2 to about 60%, even more preferably from about 3 to about 40%, most preferably above 10%. In liquid or paste compositions of the invention, the amorphous silica of the invention is preferably present in an amount of from about 1 to about 30% by weight, more preferably from about 5 to about 25%.

The oral compositions of the invention may contain one or more additional components, as will now be described.

Oral compositions of the invention preferably comprise one or more surfactants, preferably selected from anionic, nonionic, amphoteric and zwitterionic surfactants, and mixtures thereof, all being suitable for dental and/or oral use.

Suitable anionic surfactants may include soaps, alkyl sulphates, alkyl ether sulphates, alkaryl sulphonates, alkanoyl isethionates, alkanoyl taurates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Example of preferred anionic surfactants may include sodium lauryl sulphate, sodium dodecylbenzene sulphonate, sodium lauroyl sarcosinate and sodium coconut monoglyceride sulphonate.

Nonionic surfactants which may be suitable for use in composition of the invention include sorbitan and polyglycerol esters of fatty acids, as well as ethylene oxide/propylene oxide block copolymers.

Amphoteric surfactants which may be suitable for use in compositions of the invention include betaines such as cocamidopropyl betaine, and sulphobetaines, for example.

The surfactant(s) may be present in the oral composition of the invention in a total amount of from about 0.1 to about 3% by weight.

Water is another preferred component of the oral compositions of the invention and may be present in an amount of from about 1 to about 90% by weight, preferably from about 10 to about 60%, more preferably from about 15 to about 50% and most preferably for clear pastes from about 1 to about 20%.

Toothpastes and creams of this invention may also contain humectants, for example polyols such as glycerol, sorbitol syrup, polyethylene glycol, lactitol, xylitol and hydrogenated corn syrup. The total amount of humectant, if present, may be for example in the range of from about 10 to about 85% by weight of the composition.

In the oral compositions of the present invention it is particularly preferred that one or more thickening agents and/or suspending agents are included, in order to give the composition the desired physical properties (e.g. whether a paste, cream or a liquid) and in order that the amorphous silica of the invention remain stably dispersed throughout the composition.

A particularly preferred means for thickening the oral compositions of the invention is by the inclusion of conventional thickening materials such as thickening silicas, examples of which have already been mentioned above.

Other suitable suspending/thickening agents are well known in the art and include for example polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof), heteropolysaccharide gums such as xanthan and guar gums, and cellulose derivatives such as sodium carboxymethyl cellulose.

Particularly suitable thickening agents are xanthan gum and sodium carboxymethyl cellulose.

The thickening agent and/or suspending agent (which may be used singly or as mixtures of two or more such materials) may be present in the composition in a total amount of from about 0.1 to about 50% by weight; preferably from about 0 to about 15%, most preferably from about 1 to about 10% for silica thickening agents; preferably from about 0.1 to about 5% for polymer suspending agents.

The compositions of the invention may contain one or more other components conventionally found in oral compositions. Suitable additional ingredients include: flavouring substances, e.g. peppermint, spearmint; artificial sweeteners; perfume or breath freshening substances; pearlescing agents; peroxy compounds, e.g. hydrogen peroxide or peracetic acid; opacifiers; pigments and colourings; preservatives; moisturising agents; fluoride-containing compounds; anti-caries agents; anti-plaque agents; therapeutic agents such as zinc citrate, Triclosan (ex Ciba Geigy); proteins; salts; pH adjusting agents.

Compositions in accordance with the present invention may be made by conventional methods of preparing oral compositions. Pastes and creams may be prepared by conventional techniques, for example using high shear mixing systems under vacuum.

SPECIFIC DESCRIPTION OF THE INVENTION

The invention will be further described in the following examples.

A heated stirred reaction vessel was used for the silicate/acid reaction.

Mixing is an important feature in the reaction of silicate and sulphuric acid. Consequently fixed specifications, as listed in Chemineer Inc. Chem Eng. Apr. 26 1976 pages 102–110, have been used to design the baffled, heated stirred reaction vessel. Whilst the turbine design is optional to the mixing geometry, a 6-bladed 30° pitched bladed unit has been chosen for the experiments in order to ensure maximum mixing effectiveness with minimum shear.

EXAMPLES 1 & 2

The solutions used in the process were as follows:

a) Sodium silicate solutions with a $SiO_2:Na_2O$ molar ratio in the range of 2.1 to 2.5:1 and a solids content in the range of 17.0 to 21.5% by weight.

b) A sulphuric acid solution of specific gravity 1.10 (15% w/w solution) to 1.14 (20% w/w solution).

The following procedure was adopted in the preparation of the precipitated silicas. Values of reactant concentrations, volumes, temperatures and ageing steps are given in Table 1.

(A) liters of water were placed in the vessel with (B) litres of sodium silicate solution. This mixture was then stirred and heated to (C) °C.

(D) liters of sodium silicate and (F) litres of sulphuric acid were then simultaneously added over 60 minutes at (C) °C. The flow rates of the silicate and acid solutions were uniform throughout the addition period to ensure that a constant pH, in the range from 8.0 to 9.0 was maintained in the vessel.

The resultant slurry was aged for (G) minutes at (C) °C.

Sulphuric acid solution was then added over a period of (H) minutes to pH 5. The slurry was then aged for (J) minutes at pH 5 and (C) °C. The slurry was then adjusted to the final end of batch pH (K).

The final slurry was then filtered and washed with water to remove excess electrolyte. Typically, for a toothpaste application, the residual electrolyte would be less than 2% on a dry weight basis. After washing, the filter cake in each example was flash dried to remove the water rapidly from the silica so that the structure is maintained, and comminuted to the desired particle size range.

The precipitated silicas obtained had the properties expressed on a dry weight basis listed in Table 2.

TABLE 1

| TEST | EX. 1 | EX. 2 |
| --- | --- | --- |
| Vessel Capacity (liters) | 64 | 64 |
| Water Volume (A) (liters) | 17.2 | 18.6 |
| Silicate ratio $SiO_2/Na_2O$ by wt. | 2.21 | 2.23 |
| $SiO_2$ Concentration in Silicate (% w/w) | 13.99 | 14.41 |
| Silicate volume (B) (liters) | .32 | .31 |
| Silicate volume (D) (liters) | 26.8 | 25.9 |
| Acid concentration (% w/w) | 17.5 | 17.2 |
| Acid volume (F) (liters) | 15.7 | 15.3 |
| Temperature (C) (° C.) | 98 | 98 |
| Acid II addition time (H) (mins.) | 5 | 1 |
| Post sol age (G) (mins.) | 10 | 0 |
| Age at pH 5 (J) (mins.) | 10 | 0 |
| End of batch pH (K) | 5 | 3 |

TABLE 2

| TEST | EX. 1 | EX. 2 |
| --- | --- | --- |
| RDA value | 51 | 64 |
| Max. % Transmission | 94 | 93 |
| At Refractive Index of | 1.45 | 1.45 |
| Oil Absorption ($cm^3/100$ g) | 125 | 115 |
| pH | 6.2 | 6.6 |
| Weight Mean Particle Size ($\mu$m) | 7.3 | 9.3 |
| Moisture loss at 105° C. | 4.5 | 3.8 |
| Ignition Loss at 1000° C. | 8.5 | 8.1 |
| Surface Area ($m^2$/g) | 75 | 105 |
| $SO_4^{2-}$ (%) | 0.1 | 0.14 |
| $Cl^-$ (%) | 0.01 | 0.004 |
| Loose Bulk Density (g/l) | 220 | 240 |
| Hg Pore Volume ($cm^3$/g) | 1.53 | 1.3 |
| Mean Pore Diameter (nm) | 81.6 | 49.5 |
| Skeletal Density (g/$cm^3$) | 2.171 | 2.1125 |

After firing at 1100° C., the product was in the form of alpha cristobalite.

EXAMPLES 3 & 4

The amorphous silica prepared as described in Ex. 1 was formulated at 10 and 20% loading to produce an opaque dentifrice formulation. The toothpastes had commercially suitable properties for stability and usage, low RDA values and good cleaning properties, they were found to be particularly suitable for preventing stain formation and they did not damage teeth.

| INGREDIENT | EXAMPLE 3 LOADING (% w/w) | EXAMPLE 4 LOADING (% w/w) |
| --- | --- | --- |
| Water | 36.18 | 39.18 |
| Sorbitol | 25.0 | 25.0 |
| Glycerol | 10.0 | 10.0 |
| Silica of the Invention (Ex. 1) | 20.0 | 10.0 |
| Sorbosil TC15 (*) | 3.0 | 10.0 |
| SLS | 1.5 | 1.5 |
| PEG 600 | 1.2 | 1.2 |
| Flavour | 1.0 | 1.0 |
| Xanthan Gum | 0.9 | 0.9 |
| TiO2 | 0.7 | 0.7 |
| NaF | 0.32 | 0.32 |
| Saccharin | 0.2 | 0.2 |
| RDA Value of toothpaste | 48 | 35 |

(*Sorbosil TC15 is a thickening silica produced by Crosfield Ltd)

EXAMPLE 5

Example 1 was also formulated into the following transparent dentifrice formulation:

| INGREDIENT | LOADING (% w/w) |
| --- | --- |
| Sorbitol | 66.0 |
| Silica of the Invention | 20.0 |
| Water | 6.8 |
| Sorbosil TC15 (*) | 2.0 |
| SLS | 1.5 |
| PEG 600 | 1.2 |
| Flavour | 1.0 |
| SMFP | 0.8 |
| SCMC | 0.5 |
| Saccharin | 0.2 |

(*Sorbosil TC15 is a thickening silica produced by Crosfield Ltd)

This produced an exceptionally visually clear paste with refractive index 1.451 which was stable with time and had good cleaning properties, similar to those exhibited by toothpaste formulations containing higher abrasive silicas. The clarity number, as given using the RIT 4-74 chart was +13.

We claim:

1. Amorphous silica which comprises:
   an RDA value of between 30 and 70;
   an oil absorption capacity of between 100 and 155 $cm^3$/100 g; and
   a BET surface area of up to 200 $m^2$/g.

2. Amorphous silica according to claim 1 in which the RDA value is between 40 and 70.

3. Amorphous silica according to claim 1 in which the RDA value is between 50 and 60.

4. Amorphous silica according to claim 1 in which the oil absorption capacity is between 100 and 145 $cm^3$/100 g.

5. Amorphous silica according to claim 1 in which the oil absorption capacity is between 115 and 130 $cm^3$/100 g.

6. Amorphous silica according to claim 1 having a light transmission of more than 70% at a refractive index within the range of 1.445 to 1.456.

7. Amorphous silica according to claim 6 having a peak of light transmission in the refractive index range of 1.445 to 1.456.

8. Amorphous silica according to claim 1 having a mercury pore volume of above 1 $cm^3$/g.

9. Amorphous silica according to claim 1 having a mercury pore volume of above 1.2 $cm^3$/g.

10. Amorphous silica according to claim 1 having a Mean Pore Diameter between 25 and 100 nm.

11. Amorphous silica according to claim 10 having a Mean Pore Diameter above 40 nm.

12. Amorphous silica according to claim 1 having a structural water content of between 3.5 and 5.0%, a BET surface area of 50 to 200 $m^2$/g, a pH in a 5% solution of between 6 and 7.5, a loose bulk density of between 180 and 300 g/l, and a skeletal density of above 2.1 g/$cm^3$.

13. Amorphous silica according to claim 12 having a structural water content of between 4.0 and 4.5%.

14. Amorphous silica according to claim 12 having a BET surface area of 50 to 150 $m^2$/g.

15. Amorphous silica according to claim 12 having a loose bulk density of between 200 and 250 g/l.
    eb;normal 16. Process for the production of amorphous silicas having an RDA value of between 30 and 70; an oil absorption capacity of between 100 and 155 $cm^3$/100 g; and a BET surface area of up to 200 $m^2$/g, said process comprising:
   a) adding a 17.0 to 21.5% solution of 2.1 to 2.5 Molar Ratio silicate solution to water,
   b) then further adding a 17.0 to 21.5% solution of 2.1 to 2.5 Molar Ratio silicate solution together with a 15 to 20% sulfuric acid solution, over period of over 40 minutes at such flow rates that the pH is maintained in the range from 8.0 to 9.0, c) then aging the resultant slurry for a perod of 0 to 30 minutes at a temperature of 90 to 100° C., d) doing a second addition to a 15 to 20% sulfuric acid solution to bring the pH down to pH 3 to 5, e) aging the resulting slurry for a period of 0 to 20 minutes at pH 5 at a temperature of between 90 and 100° C., f) adjusting the pH to pH 3.5 to 5, and g) eventually filtering, washing and drying the final slurry.

17. Process as claimed in claim 16 in which the addition of said silicate solution together with the sulfuric acid solution is made over a period of less than 80 minutes.

18. Process as claimed in claim 16 in which the first aging step is carried out over a period of 8 to 12 minutes.

19. Process as claimed in claim 16 in which the second aging step is carried out over a period of 8 to 12 minutes.

* * * * *